United States Patent [19]

Cremers et al.

[11] Patent Number: 4,544,274

[45] Date of Patent: Oct. 1, 1985

[54] APPARATUS AND METHOD FOR MEASUREMENT OF WEAK OPTICAL ABSORPTIONS BY THERMALLY INDUCED LASER PULSING

[75] Inventors: David A. Cremers; Richard A. Keller, both of Los Alamos, N. Mex.

[73] Assignee: The United States of America as represented by the United States Department of Energy, Washington, D.C.

[21] Appl. No.: 386,372

[22] Filed: Jun. 8, 1982

[51] Int. Cl.$^4$ .............................................. G01N 21/00
[52] U.S. Cl. .................................................... 356/436
[58] Field of Search ................ 356/432, 436; 250/343; 372/51, 53, 107, 108

[56] References Cited

PUBLICATIONS

Andrews, C. L., *Optics of the Electromagnetic Spectrum*, Prentice-Hall Inc., 1960, pp. 352–355.
Gordon et al., "Long-Transient Effects in Lasers with Inserted Liquid Samples" J. Appl. Phys. 36, 3 (1965).
Cremers et al., Abstract WJ6 in the Advance Program for the Conference on Lasers and Electro-Optics (CLEO '81), Washington, DC, Jun. 10–12, 1981.
Solimini, D., "Accuracy & Sensitivity of the Thermal Lens Method for Measuring Absorption", *Applied Optics*, vol. 5, No. 12, (Dec. 1966), pp. 1931–1939.
Dovichi et al., "Time-Resolved Thermal Lens Calorimetry", *Analyt Chem.*, vol. 53 (1981), pp. 106–109.
Jackson et al., "Photothermal Deflection Spectroscopy and Detection" *Applied Optics*, vol. 20, No. 8, (Apr. 15, 1981), pp. 1333–1344.

*Primary Examiner*—R. A. Rosenberger
*Attorney, Agent, or Firm*—Samuel M. Freund; Paul D. Gaetjens; Judson R. Hightower

[57] ABSTRACT

The thermal lensing phenomenon is used as the basis for measurement of weak optical absorptions when a cell containing the sample to be investigated is inserted into a normally continuous-wave operation laser-pumped dye laser cavity for which the output coupler is deliberately tilted relative to intracavity circulating laser light, and pulsed laser output ensues, the pulsewidth of which can be related to the sample absorptivity by a simple algorithm or calibration curve. A minimum detection limit of less than $10^{-5}$ cm$^{-1}$ has been demonstrated using this technique.

15 Claims, 6 Drawing Figures

APPARATUS AND METHOD FOR MEASUREMENT OF WEAK OPTICAL ABSORPTIONS BY THERMALLY INDUCED LASER PULSING

This invention is the result of a contract with the Department of Energy (Contract No. W-7405-ENG-36).

BACKGROUND OF THE INVENTION

The present invention relates generally to the measurement of weak optical absorptions and more particularly to the use of the thermooptic effect which occurs when a laser beam traverses a weakly absorbing solution forming a negative thermal lens which lens, when automatically correcting for a deliberate optical misalignment of a laser cavity into which the sample under investigation is inserted, causes pulsed operation in what would normally be continuous laser output, the pulsewidth of this output being related to the sample absorptivity.

When a laser beam traverses a weakly absorbing solution a negative thermal lens is formed in the solution due to heating of the liquid. This is one manifestation of the thermooptic effect, and it can be used to measure small absorptivities, $\alpha$, of solutions or molar extinction coefficient of solutes, $\epsilon_s = \alpha_s/c$, where $\alpha_s$ is the absorptivity of the solute and c is the solute concentration in a particular solvent. A cell containing the solution to be studied is inserted into the cavity of a normally continuous-wave dye laser. If the plane of the output coupler of the laser is intentionally misaligned slightly, the laser begins pulsed operation at a frequency essentially independent of $\alpha$ and only slightly dependent on the extent of the cavity misalignment. The pulses are equally spaced and have identical pulsewidths which width is strongly dependent on the absorptivity of the sample solution. Such pulsewidths may decrease by as much as a factor of 100 as the absorptivity is increased making this characteristic useful for measuring weak absorptivities of solutions.

The thermooptic phenomenon has been known for many years, and has been used for almost as many years for absorption measurements. Reference 1 describes transient effects in lasers with liquid samples inserted in the laser cavity, but the method and apparatus of the instant invention utilizes a different manifestation of the thermooptic effect from other previous absorption measurement techniques or this transient-based method.

1. In "Long-Transient Effects in Lasers with Inserted Liquid Samples," by J. P. Gordon, R. C. C. Leite, R. S. Moore, S. P. S. Porto and J. R. Whinnery, J. Appl. Phys. 36, 3 (1965), the buildup and decay of the output of a helium-neon laser when absorbing liquids were placed within its resonator cavity is described. The application of the authors' method to measurement of small absorbances is mentioned although not elaborated upon. The transient buildup and decay of the laser output takes place over a timescale of several seconds and appears to be explainable by the simple heating of the liquid with the formation of a thermal lens which simply either improves or causes the deterioration of the laser cavity alignment, thereby effecting its output. The effect could not be correctly described as a laser oscillatory or pulsed operation as occurs in our invention. Further, their system, unlike ours, works better when operated near the threshold of stable laser action. Moreover, the intentional misalignment of the cavity output coupler which gives rise to the approximately 5 Hz oscillation in output of the instant invention is not taught by this reference. That is, the advantage of having a repetitive and highly reproducible laser signal which can be easily related to the sample absorptivity in that such signals are readily treated using standard detection and averaging techniques to achieve the maximum signal-to-noise ratio and therefore the greatest measurement sensitivity and range is not deducible from the Gordon et al. paper.

2. In "Time-Resolved Thermal Lens Calorimetry," by N. J. Dovichi and J. M. Harris, Anal. Chem. 53, 106 (1981), the authors describe a kinetic approach to measurements involving the thermal lens generation in weakly absorbing liquids. Therein it is explained that obtaining quantitative information from the time dependence of the signal derived from pulsing or chopping the heating laser is more efficient and reproducible than simply measuring the initial and final signal amplitudes alone with a long time delay in between these two sampling points. It is also pointed out that the signals obtained are more readily analyzed if one samples the output from the sample cell at short times since the thermal lens formed will then be relatively thin. No mention is made of intracavity insertion of the sample, with consequent oscillation of the laser output, however, as is described in the instant invention.

3. A more theoretical discussion of the time-resolved thermooptic phenomenon is found in "Photothermal Deflection Spectroscopy and Detection," by W. B. Jackson, N. M. Amer, A. C. Boccara, and D. Fournier, Appl. Optics 20, 1333 (1981). The authors describe the most common working embodiments of the thermooptic detection technique known in the art and show them schematically in their FIG. 4. As in Ref. 2, no mention is made of intracavity gain modulation by an absorbing medium under investigation.

References 1-3 then, provide no guidance for one skilled in the art to derive the method and apparatus of the instant invention. In particular, the observed laser oscillation and the relationship between the pulsewidth and the intracavity sample absorptivity represent a new thermooptic phenomenon based on the well-known negative thermal lens formation in laser heated materials.

4. The instant inventors have published a brief abstract which is not an enabling disclosure. In "Measurement of Weak Optical Absorptions by Thermally Induced Laser Pulsing," by David A. Cremers and Richard A. Keller, Conference on Lasers and Electro-optics Advance Program, Washington, D.C., June 10-12, 1981 distributed sometime in April, 1981, the authors mention pulsed laser operation when a weakly absorbing solution is introduced into a misaligned continuous-wave dye laser cavity. However, the key optical component which must be misaligned, and in what manner is not described. For example, a misalignment of the output coupler of the dye laser cavity in a horizontal direction when the folding mirrors are vertically situated will *not* produce pulsed operation, nor will any misalignment of the sample containing intracavity cell.

SUMMARY OF THE INVENTION

An object of the instant invention is to determine the absorptivity of samples.

Another object is to determine the absorptivity of solutes in liquid or solid solution.

Yet another object is to determine the solute concentration in liquid and solid solutions.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus of this invention may comprise a cavity of a normally continuous-wave laser into which a cell containing the sample under investigation is inserted and which has its output coupler deliberately tilted relative to laser light circulating within the cavity such that stable, pulsed laser output is obtained in place of continuous-wave oscillation. Preferably, such laser cavity includes a continuous-wave laser-pumped dye laser cavity. It is also preferred that such cavity further comprises an end mirror, a beam folding mirror, a dye solution jet stream placed in between the beam folding mirror and the end mirror, an aperture placed in front of the beam folding mirror, and a Lyot filter for selection of the wavelength of the dye laser cavity output. A light transmitting cell containing the solution or material under investigation is inserted into the dye laser cavity in between the output coupler and the Lyot filter, and is oriented at approximately Brewster's angle relative to circulating laser light. The dye solution jet stream is excited by a continuous-wave pump laser which, were it not for the tilted output coupler, would ordinarily cause continuous-wave-dye laser output. However, the tilt of the output coupler causes pulsed laser output, essential to the operation of the instant invention, the width of the output pulses bearing an inverse linear relationship to the absorptivity of the sample. It is preferred that the angle of tilt of the output coupler relative to the circulating laser light be such that it is the largest angle away from normal incidence that will support stable, pulsed laser operation, and in the plane of the position of the remaining optical components of the cavity. Preferably also, very high reflectance output couplers are used to further improve the stability of the pulsed cavity output by increasing the circulating intracavity laser radiation. This cavity output is detected, amplified, averaged and recorded using conventional, commercially available electronics. The pulsewidth determination derivable therefrom is a measure of the sample absorptivity.

In a further aspect of the present invention, in accordance with its objects and purposes, the method hereof may also comprise inserting a cell containing a liquid or solid solution of the solute for which absorotivity or concentration information is required, or a pure liquid or solid for which a value for the absorptivity is sought into the cavity of a normally continuous-wave output laser, the output coupler of which is deliberately misaligned to induce pulsed laser operation which consists of equally-spaced output pulses having identical pulsewidths resulting from the thermal lensing phenomenon occurring inside the sample cell due to the interaction of the sample with laser radiation circulating within the cavity, and measuring the pulsewidth which can be related to the sample absorptivity. An algorithm is used to extract the absorptivity of a pure liquid or solid from measured pulsewidths and values of the average intracavity circulating laser power. To obtain solute concentration or absorptivity information, calibration curves of pulsewidth versus concentration of the solute in a solution using the same solvent as the unknown solution, or pulsewidth versus absorptivity for a solution of a solute of known absorptivity in the same solvent as the solution under investigation, respectively, both with the source cell pathlength, are first generated. The unknown concentration or absorptivity is then simply read from the appropriate curve corresponding to the measured pulsewidth of the solution under investigation. It is preferred that this cavity includes a laser-pumped, continuous-wave dye laser cavity. It is also preferred that the output coupler be tilted relative to the direction of the circulating intracavity laser radiation at the maximum angle that will sustain stable pulsed operation of the dye laser, and in the plane of the other laser cavity components.

In summary, then, the apparatus and method of the present invention exploits the thermal lensing phenomenon to convert a continuous-wave operation laser-pumped dye laser to pulsed output when a sample cell containing a substance to be investigated is inserted into the dye laser cavity, and the output coupler is deliberately misaligned relative to intracavity circulating laser light. The pulsewidth of this output is a measure of the absorptivity of the sample and can be used to determine this quantity and for evaluating the concentration of a solute in solution. Advantages of the instant invention are (1) modest equipment requirements; (2) simple measurements with no critical laser alignments; (3) good reproducibility; and (4) high sensitivity.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION OF THE PREFERRED EMBODIMENT

If a cell containing a weakly absorbing solution is subjected to laser radiation, changes occur in the illuminating beam as it passes through the cell. Such changes are a manifestation of the thermooptic effect, and are related to the heating of the liquid in the region traversed by the laser beam. Generally, if the absorbed laser power is sufficiently small, a simple negative thermal lens which defocuses the laser beam is formed in the liquid. This lens results from very small variations in refractive index of the liquid across the beam due to the heating. If a cell containing a sample to be investigated is positioned at Brewster's angle in the cavity of a normally continuous-wave operation laser-pumped dye laser for which the output coupler is tilted slightly off-axis relative to intracavity circulating laser light, the dye laser goes into a pulsed mode of operation. If the output coupler is not tilted, the presence of a solution having finite absorption in the cell causes a blooming of the continuous wave laser output, or may even extinguish the laser oscillation. The laser output in the above-mentioned pulsed mode of operation, consists of a series of equally-spaced pulses having identical pulsewidths. The pulse frequency, which generally lies between 3 and 10 Hz for all solutions investigated, is relatively independent of sample absorptivity. Similarly, it is only slightly dependent upon the cavity alignment. The pulsewidth, on the other hand, is strongly dependent upon the absorptivity of the sample, and may decrease by as much as a factor of 100 as the absorptivity is increased. This phenomenon has been used to measure an absorptivity of less than $10^{-5}$ cm$^{-1}$, while other techniques based on the thermooptic affect have been used to determine absorptivities in the range $10^{-3}$–$10^{-5}$ cm$^{-1}$.

Reference will now be made in detail to the present preferred embodiment of the invention, an example of which is illustrated in the accompanying drawings.

Figure 1:
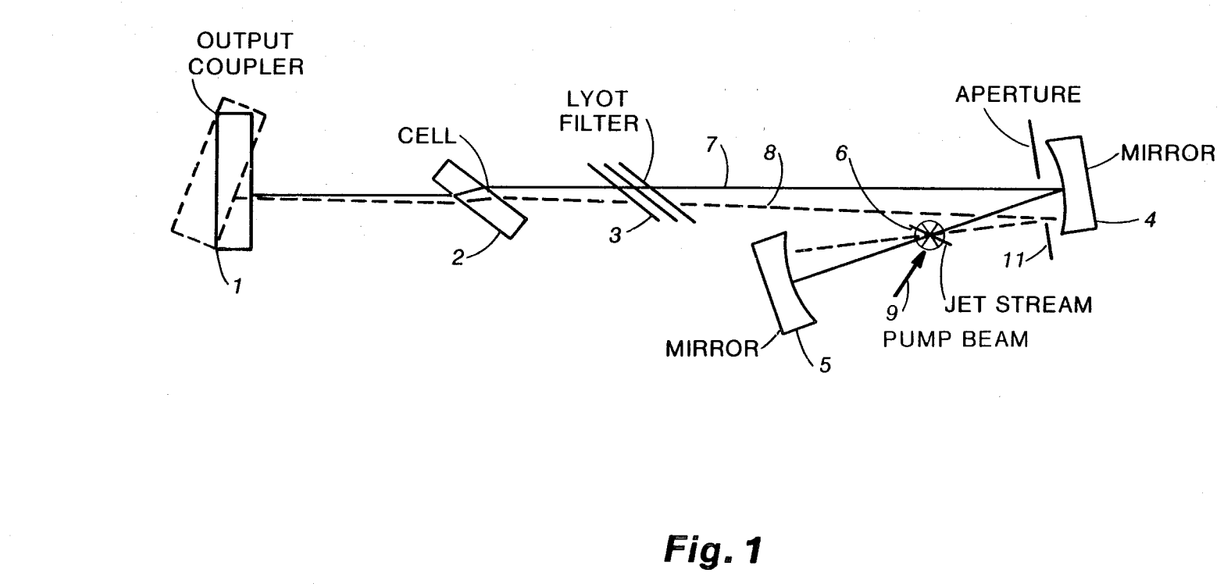
FIG. 1 is a schematic representation of the dye laser showing the tilt of the output coupler from the optimum continuous-wave operation optical path.

FIG. 1 shows the components of the normally continuous-wave laser-pumped jet stream dye laser cavity, which is the basis of the apparatus of the instant invention. A sample cell 2 is inserted in between an output coupler 1 and a Lyot filter 3. For small cells, the entire cell can be oriented in such a manner that parallel laser radiation transmitting windows between which the sample under investigation is located are situated at approximately Brewster's angle relative to intracavity circulating laser radiation. Longer cells, necessary for measurement of extremely small absorptivities, are oriented with the body of the cell along the intracavity circulating laser radiation, while the laser transmitting end windows, between which the sample lies, are individually located at Brewster's angle, to minimize reflective losses to the intracavity laser radiation which necessarily traverses the cell. A folding mirror 4 and an end mirror 5 complete the optical components necessary for laser operation, and surround the continuous-wave laser-pumped jet stream 6 which is schematically indicated as flowing into the plane of the figure. The pumping laser radiation 9 is shown to enter parallel to the plane of the figure. In normal operation, the circulating laser radiation inside the dye laser cavity 7 impinges upon the output coupler 1 in normal incidence. However, the apparatus and method of the instant invention requires a slight tilt of the output coupler in the vertical direction which shifts the beam along the path designated schematically by the broken line 8. This induces the aforementioned pulsed operation output. It was found that a horizontal tilt of the output coupler will not result in the desired pulsed output. Preferably, the dye laser cavity is pumped with about 5.2 W of 515 nm radiation from an argon ion laser. For those experiments requiring a 10 cm path length cell with Brewster angle windows, the output coupler mirror was mounted externally to the cavity to permit insertion of the longer cell into the cavity, while for short cells, those with pathlength of the order of 1.29 cm, cell insertion could achieved without cavity modification. Stability of pulsed operation was enhanced by increasing the circulating intracavity laser power through the use of high reflectance output couplers. Reflectances of the output coupler at the two wavelengths used in the reduction to practice of our invention were 0.9989 (583 nm) and 0.9993 (633 nm). Wavelength selection was achieved by a Lyot filter 3, and preferably, the lasing dye solution was rhodamine 6 G in ethylene glycol at a concentration of about 1.5 g/l. It should be mentioned at this point that it would be obvious to one skilled in the appropriate art that the instant invention would be operable using any normally continuous-wave operation laser. A dye laser was chosen so that more than one wavelength could be investigated.

Figure 2:
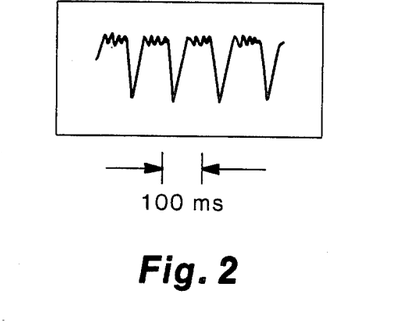
FIG. 2 is an oscilloscope trace of the detected dye laser output for an intracavity inserted sample of pure methanol.

FIG. 2 shows the dye laser output when operating in the pulsed mode where the output coupler has been deliberately misaligned and a sample of pure methanol has been inserted intracavity. It is seen that the output is a series of equally-spaced pulses having identical pulsewidths. For a fixed tilt of the output coupler, the frequency of pulsed operation is relatively constant for solutions of different total absorptivity, those with different solvents, and for changes in cavity alignment. In the majority of cases, the pulsing frequency was between 3–10 Hz, although the frequency could be controlled to a limited extent within 1–15 Hz by adjustment of the angle of tilt of the output coupler. It was found, that as the angle of tilt is reduced, the pulsing frequency increases until continuous-wave lasing is achieved. Preferably, the mirror is given the maximum angle of tilt that would sustain pulsed operation. This corresponds to about 0.9 milliradians vertically (either up or down) as measured from the mirror position at which optimum continuous-wave operation occurs. The pulsewidth, on the other hand, is strongly dependent upon the absorptivity of the sample solution and may decrease by as much as a factor of 100 as the sample absorptivity is increased. It is this fact that renders the apparatus and method of the instant invention useful for measuring weak absorptivities of solutions which can yield solute concentration information, and the absorptivities of solutes in solution and of pure liquids. Reference 1, described hereinabove, reports oscillation of laser power due to an intracavity thermal lens when the laser was operated near threshold. The stability of the oscillations of the method and apparatus of the instant invention, however, increases as the circulating laser power is increased.

Figure 3:
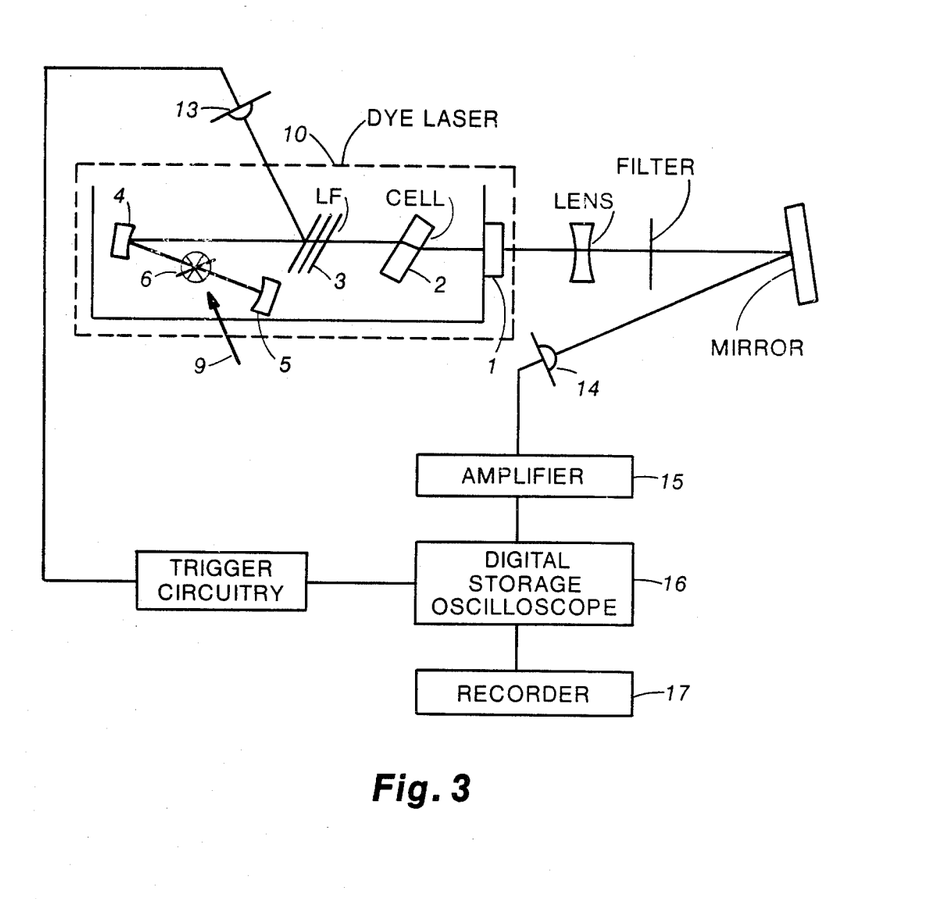
FIG. 3 is a schematic representation of the entire apparatus used to measure the pulsewidths and circulating intracavity laser power obtained from the pulsed dye laser operation.

FIG. 3 shows the entire apparatus used to record and average the pulsed operation pulsewidths. The above-described dye laser 10 is combined with commercially available electronics and optical components in order to accomplish these measurements. Attenuated dye laser output pulses are monitored by an intensity calibrated photodiode 14. The photodiode signal is amplified 15 and then averaged by a digital storage oscilloscope 16 and recorded on a hard copy recording device 17. The sweep of the signal averager was externally triggered by a second photodiode 13 positioned to intercept light reflected from the Lyot filter 3. Generally, 128 separate pulses were averaged to produce a single pulsewidth measurement. The intracavity circulating laser power was measured using the calibrated photodiode 14 to monitor the intensity of radiation transmitted by the output coupler. The power in the cavity was then calculated from the known transmittance of the mirror.

Figure 4:
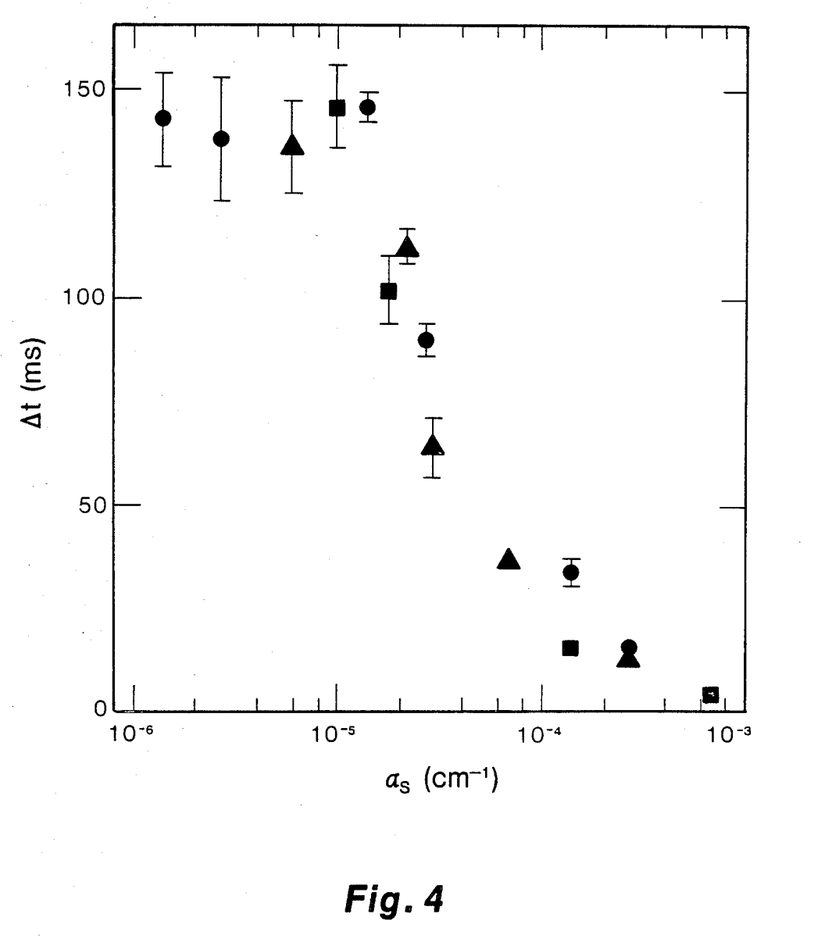
FIG. 4 is a graph of the measured pulsewidth, $\Delta t$, versus solute absorptivity, $\alpha_s$, for solutions of iodine in carbon tetrachloride, the different plotting symbols referring to measurements made on one of three days.

Solutions containing solutes of known absorptivity were used in many of the measurements. At wavelengths of 583 nm and 633 nm, the quantum yield of conversion of electronic energy into heat is essentially unity for these solutes so that all of the light absorbed is turned into heat effective in forming the thermal lens. Dilute solutions of each solute were prepared from more concentrated solutions for which the absorptivities were measured with a conventional spectrophotometer. FIG. 4 shows the results of the pulsewidth measurements made with solutions of $I_2/CCl_4$. The three different symbols depict the results taken over three separate days, and indicate the day-to-day reproducibility of the laser pulsing technique, and further, that the pulsewidth is insensitive to small variations in position of the sample cell in the cavity. Because of the low absorptivity of carbon tetrachloride, it was necessary to use a long pathlength cell to obtain steady pulsed operation. A 10 cm cell of fused pyrex with Brewster angle windows was employed for these measurements.

The pulsewidth is related to the total absorptivity of the solution at the lasing wavelength. The maximum absorptivity that can be measured with the method and apparatus of the instant invention is determined by the intracavity circulating laser power. That is, the loss introduced by the absorbing solution cannot be large enough to extinguish laser action. To be noticed in FIG. 4, for the experimental conditions of the preferred embodiment of the instant invention, lasing could not be maintained using solutions of iodine/carbon tetrachloride (contained in a 10 cm cell) having absorptivities greater than $\sim 7 \times 10^{-4}$ cm$^{-1}$. For solutions of crystal violet in methanol (contained in a 1.29 cm pathlength cell), lasing could be achieved for absorptivities of up to $\sim 10^{-2}$ cm$^{-1}$.

Figure 5:
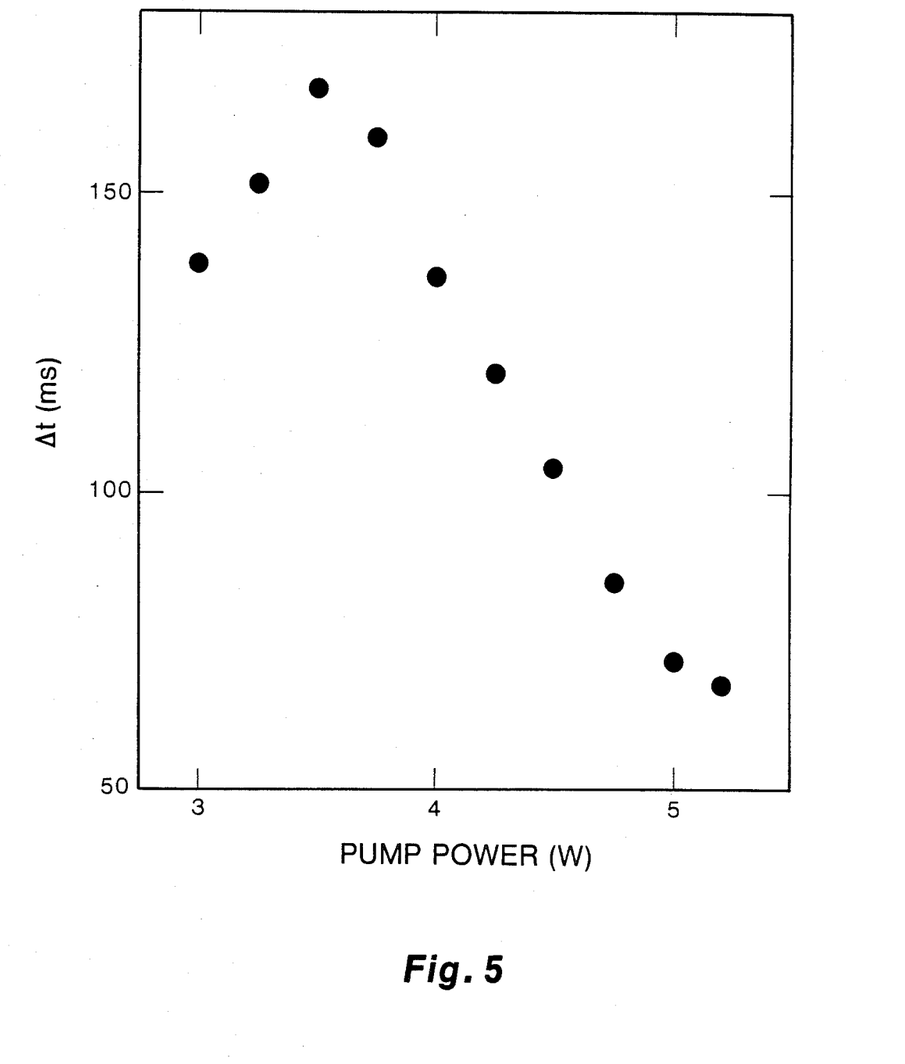
FIG. 5 shows the variation of the measured pulsewidth, $\Delta t$, with pump laser power for an intracavity sample of pure methanol; the optimum operating point being at higher pump laser powers.

FIG. 5 shows the dependence of the pulsewidth upon pump laser power for pure methanol in the sample cell. Optimal measurement conditions occurred when the laser pump power was approximately 5 watts.

Visual inspection of laser light scattered by the solution in the sample cell shows that the vertical dimension of the laser beam increases during each pulse. The change in the laser beam is best described as a spreading of the beam either up or down from the position of the beam at the start of the pulse. The direction in which the beam spreads is determined by the tilt of the output coupler mirror. For example, when the top of the mirror is tilted inward, the beam spreads upward in the cavity. On the other hand, for an outward tilt of the mirror top, the beam spreads downward during the pulse. This behavior rules out convection as a significant factor inducing pulsed operation. In both cases, the most intense portion of the spreading beam lies along the moving edge of the beam. The maximum spread of the beam in the cavity is about 1 mm. These visual observations were confirmed by measurements of the laser beam profile using a linear photodiode array. These observations suggest the mechanism by which the laser pulsing occurs. Referring again to FIG. 1, the laser axis which results in the highest power and best mode quality is designated by the solid line 7. A new lasing axis, resulting from the tilt of the output mirror 1, is designated by the dashed line 8. As the angle between these two lines is increased, the output power of the laser decreases, until an angle is reached where lasing ceases. This angle can be controlled by the aperture 11 placed in front of folding mirror 4. With the insertion of a sample cell into the cavity which has been deliberately misaligned and initially lases along the axis designated by the dashed line 8, heating begins in the sample and the beam spreads upward, with the most intense part approaching the solid line 7 until lasing ceases. This process is repeated during every pulse. The movement of the beam may be explained by noting that the formation of an off-axis, negative thermal lens in the cavity can compensate for misalignment of the planar output coupler. This can be demonstrated mathematically. The variation of cavity gain with the angle between the solid and the dashed lines also has a role in pulsed laser operation. At the start of each pulse, lasing occurs along the dashed line as described hereinabove, and the negative thermal lens formed initially will have this dashed line as its axis. The lens then produces rays which diverge from this axis both above and below. Those rays closer to the solid line experience greater gain than the rays further away. Because of this, a new thermal lens is formed around those rays in between the dashed and solid lines. There is therefore a traveling thermal lens like element in the sample which follows the upward (or downward) motion of the laser beam. It is necessary to tilt the output coupler mirror to produce pulsed operation because only in this configuration can the thermal lens like element formed in the sample correct for the misaligned cavity. In contrast, the formation of a thermal lens in a perfectly aligned cavity produces rays diverging from the solid line characterized by a reduced gain. The regenerative aspect of laser amplification does not reinforce any of these divergent rays in the aligned configuration, whereas, for the case of a tilted output coupler, rays that are closest to the solid line are preferentially amplified. The most likely processes responsible for switching the laser oscillation off, thereby producing pulsed output, may include loss of sufficient gain to sustain lasing because of spreading of the laser beam during a pulse, and the merging of the thermal lens axis with the solid line so that the lens can no longer simultaneously correct for cavity misalignment and permit lasing near or along the solid axis.

Although the thermal lens acts to produce lasing along the solid axis, where the gain is greatest, a steady-state cannot be attained along any axis in the presence of a thermal lens in the misaligned cavity. The reason for this, which also can be shown theoretically, is that in the steady state, the axis of the laser beam and the thermal lens must be coincident, and in this case the corrective power of the thermal lens is zero. For this reason, the steady state is unstable and the laser can only operate in the dynamic situation in which the axis of the thermal lens lags behind the axis of the most intense part of the laser beam. If a permanent lens were to be placed in the laser cavity to correct for the misalignment of the output coupler, continuous laser operation could be made to occur. However, the thermal lens disappears in the region behind the moving laser beam because of conductive cooling of the sample so that the corrective process cannot be permanently maintained.

Figure 6:
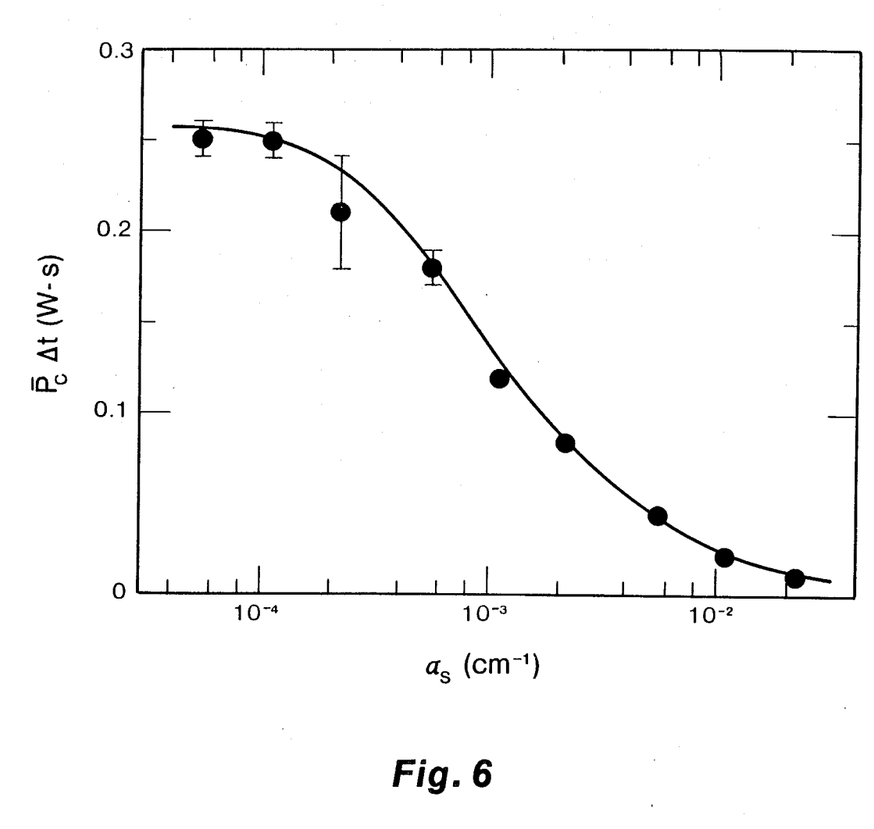
FIG. 6 is a graph of the measured pulsewidth, $\Delta t$, scaled by the average circulating laser power, $\overline{P}_c$, as a function of solute absorptivity, $\alpha_s$, for the dye crystal violet dissolved in methanol.

To illustrate the apparatus and method of the instant invention, the following examples are presented. First, however, a description is presented of how the measurements performed can be used to measure the absorptivity of samples, and to determine the concentration of a solute in solution. FIG. 6 shows a plot of $\bar{P}_c \Delta t$ versus *solute* absorptivity ($\alpha_s$) for solutions of crystal violet in methanol (absorptivity of methanol is approximately $10^{-3}$ cm$^{-1}$), where $\bar{P}_c$ is the intracavity circulating laser power at full-width at one-half-maximum of the output pulse. To be noticed is that $\bar{P}_c\Delta t$ approaches a constant value at both large and small values of $\alpha_s$. For small $\alpha_s$, the near constancy of $\bar{P}_c\Delta t$ is an indication that $\alpha_s$ is much less than $\alpha_0$, where $\alpha_0$ is the solvent absorptivity, so a small change in $\alpha_s$ will not significantly change the overall absorptivity of the sample. For large $\alpha_s$, the near constancy of the ordinate is most likely to result from the change in the mechanism responsible for turning off the laser. As the first example, the absorptivity of a pure solvent, methanol, is calculated from the data which comprises FIG. 6. The basic algorithm for performing such calculations is:

$$(\bar{P}_c\Delta t) \times (\alpha_0 + \alpha_s) = q,$$

where q is a constant. This equation can be written in a more convenient form:

$$(\bar{P}_c\Delta t)^{-1} = \alpha_s/q + \alpha_0/q = m\alpha_s + b, \quad (1)$$

where $\alpha_s$, $\alpha_0$, $\Delta t$, and $\bar{P}_c$ have all been previously defined. Using a simple linear regression calculation and the known values of $\alpha_s$, the measured values of $\bar{P}_c\Delta t$ can be fit to Eq. (1) to determine m and b. The ratio b/m is computed to find $\alpha_0$. The precision of $\alpha_0$ is $$\sigma_{\alpha_0} = \alpha_0 \left[ \left(\frac{\sigma_b}{b}\right)^2 + \left(\frac{\sigma_m}{m}\right)^2 \right]^{\frac{1}{2}}$$

and $\sigma_b$ and $\sigma_m$ are the standard deviations of the quantities b and m, respectively. The values of b, m, and $\alpha_0$ obtained for water, methanol, acetone, and carbon tetrachloride are listed in Table 1 along with the standard deviations ($\sigma_b$, $\sigma_m$) and the correlation coefficient ($r^2$). Published absorptivity values of these solvents at the appropriate wavelengths are also listed in this table.

The value obtained for water absorption at 583 nm using the apparatus and method of the instant invention and Eq.(1) is in good agreement with the published values. The precision of our measurement is 17%, which shows absorptivities of pure solvents can be determined accurately. The absorptivity of methanol reported in Table 1 is about five times greater than that obtained by workers using a dual beam thermal lensing apparatus. However, they suggest that their number is most likely unreliable, and should be scaled upward. See, e.g., M. S. Burberry, J. A. Morrel, A. C. Albrecht, and R. L. Swofford, J. Chem. Phys, 70, 552 (1979), which is hereby incorporated by reference. No value for the absorptivity of acetone is reported at 583 nm in the previous literature. The apparatus and method of this invention therefore can easily be used to determine accurately the absorption of a pure solvent. However, for solutions with absorptivities greater than approximately $10^{-2}$, there is difficulty in maintaining the pulsed laser operation so critical to the instant invention. This effectively establishes an upper limit to the utility of the invention. To establish an estimate of the lower detection limit for the laser pulsing technique, the absorptivity of CCl$_4$ at 633 nm was determined. A steady, pulsed laser output could not be achieved with pure carbon tetrachloride in the 1.29 cm pathlength cell used for the other measurements reported. However, stable pulsing was obtained with CCl$_4$ in a 10 cm cell. Table I shows the absorptivity of CCl$_4$ to be $(3.95 \pm 3.62) \times 10^{-6}$ cm$^{-1}$. The only previously reported value was that the absorptivity of CCl$_4$ was less than $10^{-5}$ cm$^{-1}$, which our value certainly satisfies. The low precision of our measurement is likely an indication that the weak absorption of carbon tetrachloride is marginally adequate to sustain pulsed operation even in a 10 cm cell at the reduced circulating power levels in the cavity at 633 nm compared to much higher values thereof at 583 nm. However, the data was very reproducible over a period of three days. In view of these results, a reasonable detection limit for our invention would be approximately $4 \times 10^{-6}$ cm$^{-1}$ for a 10 cm cell and the other conditions quoted.

TABLE I

Measured Absorptivities.

| solvent | wavelength (nm) | $m \pm \sigma_m$ | $b \pm \sigma_b$ | $r^{2a}$ | $10^4 \cdot \alpha_0$ (cm$^{-1}$) | $10^4 \cdot \alpha_0$(published) (cm$^{-1}$) |
|---|---|---|---|---|---|---|
| water | 583 | $(2.86 \pm 0.12) \times 10^4$ | $(3.56 \pm 0.46) \times 10^1$ | 0.985 | $12.4 \pm 2.1$ | $(10.8-14.0)^b$ |
| CH$_3$OH | 583 | $(3.58 \pm 0.03) \times 10^3$ | $(3.60 \pm 0.26)$ | 0.999 | $10.1 \pm 0.8$ | $2^c$ |
| CH$_3$COCH$_3$ | 583 | $(1.14 \pm 0.03) \times 10^5$ | $(1.98 \pm 0.09) \times 10^1$ | 0.996 | $1.74 \pm 0.12$ | — |
| CCl$_4$ | 633 | $(5.04 \pm 0.28) \times 10^2$ | $(1.99 \pm 1.71) \times 10^{-3}$ | 0.960 | $0.0395 \pm 0.0362$ | $<0.1^d$ |

[a] Correlation coefficient = $r^2$.
[b] R. C. Smith and K. S. Baker, Appl. Opt. 20, 177 (1981).
[c] R. L. Swofford, M. E. Long, M. S. Burberry, and A. C. Albrecht, J. Chem. Phys. 66, 664 (1977).
[d] J. Stone, J. Opt. Soc. Am. 62, 327 (1972).

The concentration of a solute can be determined using a calibration curve of pulsewidth (or $\bar{P}_c\Delta t$) versus solute absorptivity (or concentration) as shown in FIGS. 4 and 6. The solute concentration is then found by measuring the pulsewidth and $\bar{P}_c$ generated by the unknown solution of interest. Once a calibration curve of $\Delta t$ versus $\alpha_s$ has been prepared for a particular solute in a certain solvent, it can be used to determine the concentration of *other solutes* in the same solvent if the absorptivity and quantum yield for conversion of absorbed laser light into heat of both the unknown and calibration solutes in the solvent are known. The absorptivity measured by our invention is the product of the true absorptivity times this quantum yield. The reason for this is that in the case of weak solutions of a solute, changes in solute concentration only effect the value of the total absorptivity $\alpha_0 + \alpha_s$ which alters the strength of the thermal lens. The values of the other solution dependent parameters are constant for these weakly absorbing solutions and have the value appropriate to the pure solvent. The laser pulsing technique, then, is a sensitive and accurate method for determining absorptivities of samples and solute concentrations in solutions.

The ultimate sensitivity of the method is related to the solvent employed. In general, it may not always be possible to realize the minimum detection limit of this invention in measurements of solute absorbances because of the interference from large background solvent absorptions. The precision of the data in FIG. 6 indicates that solute absorptions of the order of 10% of the total absorptivity can be distinguished using our invention. That is, an $\alpha_s$ of approximately $10^{-4}$ cm$^{-1}$ can be measured in the presence of an $\alpha_0$ of about $10^{-3}$ cm$^{-1}$ which is the absorptivity of pure methanol. On the other hand, the data of FIG. 4 reveals that for iodine/carbon tetrachloride solutions, the smallest detectable solute absorptivity is on the order of the absorptivity of pure CCl$_4$ ($3.95 \times 10^{-6}$ cm$^{-1}$), rather than 10% of this value. The reduction in the ability to resolve solute absorptions is the result of a decrease in the precision of the data and loss of sensitivity when measurements are made near the minimum detection limit of this technique. The extension of the apparatus and method of the instant invention to solutes dissolved in solid solutions is straightforward.

Advantages of the instant invention are: (1) modest equipment requirements; (2) measurements are simple to make with no critical alignments; (3) good reproducibility of data; and (4) high sensitivity. The best application of the instant technique appears to be the determination of solute absorptivities, which can be done rapidly and accurately, leading to solute concentrations in solution.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for measuring weak solute optical absorptivity, $\alpha_s$, using the thermal lensing phenomenon, which comprises the steps of:
   a. inserting a cell containing a solution of the solute in a chosen solvent, into the cavity of a normally continuous-wave output laser;
   b. misaligning the output coupler of said laser cavity to induce pulsed laser operation consisting of a series of equally-spaced output pulses having identical first pulsewidth, which result from the thermal lensing phenomenon occurring within said cell because of the interaction of said solution with laser radiation circulating within said cavity;
   c. measuring said first pulsewidth of said laser output pulse;
   d. establishing a calibration curve of a series of second pulsewidth measurements, $\Delta t$, versus solute absorptivity, $\alpha_s$, for said chosen solvent and a solute of known absorptivity and having unit efficiency for the conversion of absorbed laser light into heat, placed in said cell in said laser cavity; and
   e. comparing said first measured pulsewidth with said calibration curve to locate the corresponding absorptivity which is the desired solute optical absorptivity because for weakly absorbing solutions, total absorptivity depends substantially upon the solute absorptivity and the absorption of the solvent and not on the nature of the solute.

2. A method for measuring weak solvent optical absorptivity, $\alpha_o$, using the thermal lensing phenomenon, which comprises the steps of:
   a. inserting a cell containing a solution of a chosen solute of known absorptivity, $\alpha_s$, and having unit efficiency for the conversion of absorbed laser light into heat in the solvent into the cavity of a normally continuous-wave output laser;
   b. misaligning the output coupler of said laser cavity to induce pulsed laser operation consisting of a series of equally-spaced output pulses having identical first pulsewidth, $\Delta t$, which result from the thermal lensing phenomenon occurring in said cell because of the interaction of said solution with laser radiation circulating within said cavity;
   c. measuring said first pulsewidth of said laser output pulses;
   d. measuring a first intracavity circulating laser power, $\overline{P}_c$, at the full-width-at-one-half-maximum point of said pulsed laser output for said first solute absorptivity;
   e. changing said known absorptivity, $\alpha_s$, of said chosen solute in the solvent in said cell and determining another pulsewidth and another intracavity circulating laser power resulting from a change in total absorptivity, $\alpha_o + \alpha_s$;
   f. repeating said changing of said known absorptivity of said chosen solute in the solvent in said cell step and said determining of laser pulsewidth and said intracavity circulating laser power to obtain a plurality of said laser pulsewidth and said intracavity laser power measurements; and
   g. relating said pulsewidth and said intracavity laser power measurements and said known solute absorptivity to the solvent absorptivity according to the formula $(\alpha_o + \alpha_s) \overline{P}_c \Delta t = $ constant, from which $\alpha_0$ and said constant can be extracted by mathematical curve-fitting.

3. A method for measuring unknown solute concentration in weakly absorbing solid or liquid solutions using the thermal lensing phenomenon, which comprises the steps of:
   a. inserting a cell containing the solution into the cavity of a normally continuous-wave output laser;
   b. misaligning the output coupler of said laser cavity to induce pulsed laser operation consisting of a series of equally-spaced output pulses having identical first pulsewidth, which result from the thermal lensing phenomenon occurring within said cell because of the interaction of said solution with laser radiation circulating within said cavity;
   c. measuring said first pulsewidth of said laser output pulse;
   d. establishing a calibration curve of a series of second pulsewidth measurements, $\Delta t$, versus solute concentration using the same solvent and solute as exist in the unknown solution; and
   e. comparing said first measured pulsewidth with said calibration curve to locate the corresponding solute concentration which is the desired unknown solute concentration.

4. A method for measuring solute molar extinction coefficients, $\epsilon_s$, using the thermal lensing phenomenon, for solutions of known solute concentration, c, and where the quantum yield for conversion of absorbed laser light into heat for the solute, $\Phi$, is known, which comprises the steps of:

a. inserting a cell containing a solution of the solute in a chosen solvent into the cavity of a normally continuous-wave output laser;

b. misaligning the output coupler of said laser cavity to induce pulsed laser operation consisting of a series of equally-spaced output pulses having identical first pulsewidth, which result from the thermal lensing phenomenon occurring within said cell because of the interaction of said solution with laser radiation circulating within said cavity;

c. measuring and recording said first pulsewidth of said laser output pulse;

d. establishing a calibration curve of a series of second pulsewidth measurements, $\Delta t$, versus solute absorptivity, $\alpha_s$, for said chosen solvent and a solute of known absorptivity and having unit efficiency for the conversion of absorbed laser light into heat placed in said laser cavity;

e. comparing said first measured pulsewidth with said calibration curve to locate the corresponding measured absorptivity which is the measured optical absorptivity of the solute of interest because for weakly absorbing solutions, total absorptivity depends substantially upon the solute absorptivity and the absorption of the solvent and not on the nature of the solute; and f. extracting the molar extinction coefficient, $\epsilon_s$, from the relationship $\epsilon_s = \alpha_m / \Phi c$, where $\alpha_m$ is said measured optical absorptivity of the solute of interest obtained from said calibration curve.

5. The method as described in claims 1, 2, 3, or 4, wherein said laser cavity includes a continuous-wave laser-pumped dye laser cavity.

6. The method as described in claim 5, wherein said laser cavity output coupler misaligning step gives said output coupler the maximum angle of tilt relative to the direction of said circulating laser radiation that will sustain said pulsed laser operation.

7. An apparatus for measuring weak optical absorptivity of pure samples, and of solutes in liquid and solid solution, the concentration of a solute in liquid and solid solutions, and the molar extinction coefficient of a solute in liquid and solid solutions, which comprises in combination:

a. a normally continuous-wave output laser, the cavity of which further comprises:
 i. an output coupler which is tilted relative to laser radiation circulating within said cavity such that stable pulsed laser output is obtained in place of normally continuous-wave output, the pulsewidth of which is related to the total absorptivity of the material under investigation; and
 ii. a light-transmitting cell through which said circulating intracavity laser radiation passes and which contains the material under investigation;

b. means for quantitatively detecting said laser pulsewidth and the average intracavity circulating laser power $\bar{P}_c$; and c. means for recording output from said detecting means.

8. The apparatus as described in claim 7, wherein said normally continuous-wave output laser includes a laser-pumped, normally continuous-wave output dye laser, which further comprises:

i. an output coupler which is tilted relative to laser radiation circulating within said cavity such that stable pulsed dye laser output is obtained in place of normally continuous-wave output;

ii. a beam folding mirror;

iii. an end mirror; approximately Brewster's angle relative to said circulating laser light; and vii. a continuous-wave pump laser to excite said dye solution.

9. The apparatus as described in claim 8, wherein said dye solution is introduced into said dye laser in a continuous jet stream.

10. The apparatus as described in claim 9, wherein said wavelength selection means includes a Lyot filter.

11. The apparatus as described in claim 10, wherein an aperture is placed in front of said beam folding mirror to control the mode structure of said intracavity circulating laser radiation.

12. The apparatus as described in claim 11, wherein said output coupler has a reflectance in excess of about 0.99 in order to enhance the stability of said pulsed output by increasing the circulating laser power within said laser cavity.

13. The apparatus as described in claim 12, wherein said pump laser includes an argon-ion laser operating at about 515 nm and producing approximately 5 W of power.

14. The apparatus of claim 13, wherein said dye solution includes rhodamine 6G in ethylene glycol at a concentration of about 1.5 g/l.

15. The apparatus as described in claims 7 or 14, wherein said tilted output coupler is given the maximum angle of tilt that will sustain said pulsed output operation of said laser cavity.

* * * * *